United States Patent [19]
Takagi

[11] Patent Number: 4,818,068
[45] Date of Patent: Apr. 4, 1989

[54] SLIT APPARATUS

[75] Inventor: Kazutoshi Takagi, Setagaya, Japan

[73] Assignee: Tokyo Kogaku Kikai Kabushiki Kaisha, Tokyo, Japan

[21] Appl. No.: 212,932

[22] Filed: Jun. 29, 1988

[30] Foreign Application Priority Data

Jun. 30, 1987 [JP] Japan ............................ 62-100406[U]

[51] Int. Cl.$^4$ .............................................. G02B 26/02
[52] U.S. Cl. ..................................... 350/272; 350/271
[58] Field of Search ................... 350/271, 272; 351/214

[56] References Cited
U.S. PATENT DOCUMENTS
3,639,039 2/1972 Rhodes, Jr. .......................... 350/272

Primary Examiner—John K. Corbin
Assistant Examiner—P. M. Dzierzynski
Attorney, Agent, or Firm—Brumbaugh, Graves, Donohue & Raymond

[57] ABSTRACT

A slit apparatus has a rotatable base plate and a rotatable cam driving plate which are rotated about the same axis of rotation, but independently. The base plate is provided with slit blades for forming a slit therebetween. The slit blades are rotated together with the base plate and therefore the direction of the slit is changed. The cam driving plate is provided with a cam plate for changing slit width. The slit width is changed by rotation of the cam driving plate. A slit direction adjusting knob for driving the base plate is arranged to be coaxial with a slit width adjusting knob for driving the cam driving plate.

1 Claim, 2 Drawing Sheets

SLIT APPARATUS

BACKGROUND OF THE INVENTION

1. Field of the Invention

This invention relates in general to a slit apparatus for use in a slit illuminating optical apparatus for slit illuminating an object to be examined, or more particularly to a slit apparatus which is capable of changing or varying slit direction or width.

2. Description of the Prior Art

A slit lamp for ophthalmology or a microscope for use in performing surgical operation has a slit illuminating optical apparatus for slit illuminating an object to be examined. The slit illuminating apparatus has a slit apparatus for generating a slit light beam from light issued from a light source. The direction of rotation and width of the slit light beam must be changed, and thus a variety of slit apparatus have been proposed and carried out.

As an example of a conventional apparatus, it was known to form the apparatus with an independent knob for slit direction adjustment and an independent knob for slit width adjustment. As another example, an apparatus was known of type where the slit width is adjusted by rotating a knob for slitwidth adjustment about a drive shaft perpendicular to the light axis while the slit direction is adjusted by rotating the drive shaft about the light axis.

However, the former slit apparatus has the disadvantages that its construction is complicated and that it must be operated by two knobs which are separated from each other.

The latter slit apparatus has a disadvantage in that since the operating knob itself is rotated about the light axis and thus is not fixed, the position of the operating knob must be determined by groping for it during operation.

SUMMARY OF THE INVENTION

It is an object of the invention to provide a slit apparatus in which a slit width adjusting knob and a slit direction adjusting knob are arranged to be coaxial with each other and to be in fixed positions.

In accordance with the invention, there is provided a slit apparatus which comprises a base plate provided for rotation about an axis of rotation and having a first gear arranged along the direction of rotation; at least two guiding slots formed on said base plate so that the slots are located in opposite positions with regard to said axis of rotation and along a line perpendicular to said axis of rotation; at least two rods movable along said guiding slots, respectively; at least two slit blades, each connected to one of the rods so that each of said slit blades is movable in a direction opposite to the other and in a direction parallel to said line; cam means having a second gear arranged along the direction of rotation to cause each of said rods to move in a direction opposite to the other when said cam means is rotated about said axis of rotation; slit direction adjusting means comprising a first drive shaft perpendicular to said axis of rotation, a first driving gear meshing with said first gear, and a slit direction adjusting knob; and slit width adjusting means comprising a second drive shaft coaxial with said first drive shaft, a second driving gear meshing with said second gear, and a slit width adjusting knob.

With the above-mentioned construction when the slit direction adjusting knob is rotated, both the first and second drive shafts are rotated in the same direction and degree to cause the cam means and the base plate to rotate about the axis of rotation by the same angular degree and thereby to make an adjustment of the slit direction. However, when the slit width adjusting knob is rotated, only the second drive shaft is rotated to cause the cam means to be driven and thus to cause the rods to move in directions opposite to each other, and thereby to make an adjustment of the gap between the slit blades, that is, the slit width.

DESCRIPTION OF THE PREFERRED EMBODIMENT

Figure 1:
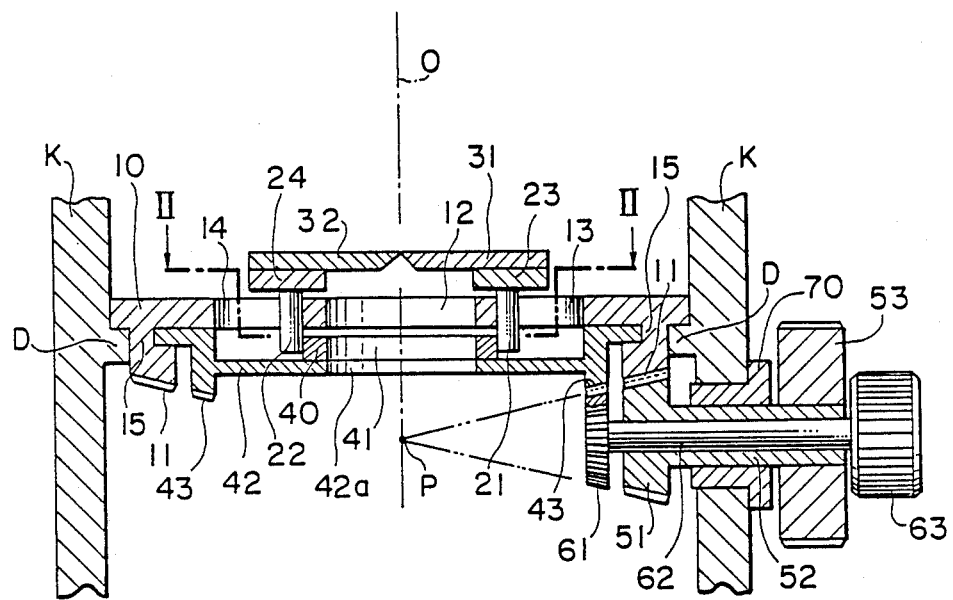
FIG. 1 is a longitudinally cross-section view showing a slit apparatus according to the invention.
Figure 2:
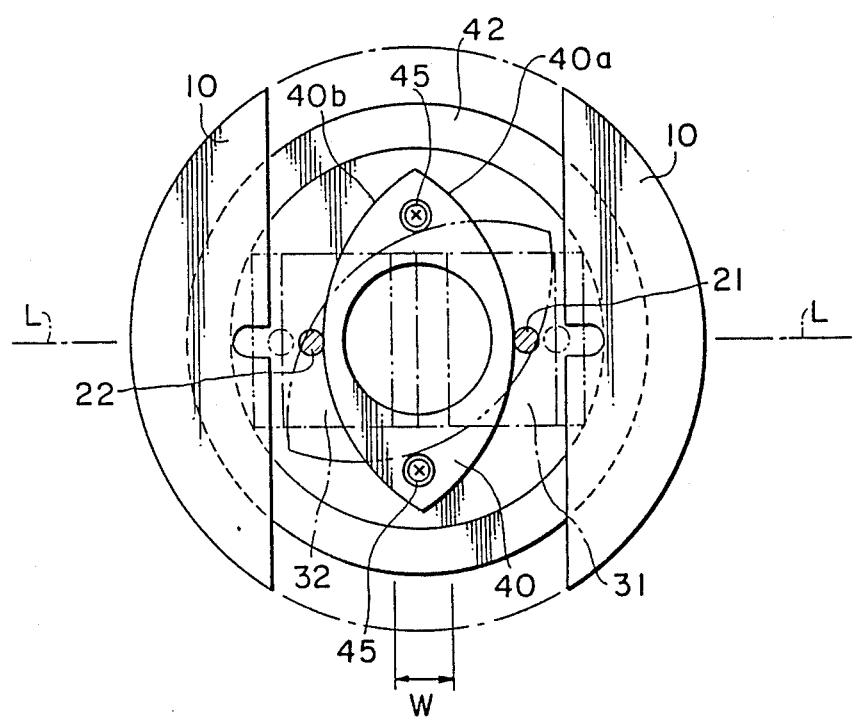
FIG. 2 is a cross-sectional view taken along the line I1—I1 of FIG. 1.

As shown in FIGS. 1 and 2, a base plate 10 is rotatably supported about an axis of rotation O by an inner flange D of a casing K. The lower surface of the base plate 10 has a bevel gear 11 which has an axis in alignment with the axis of rotation O. The base plate 10 has an opening 12 and also has linear guiding slots 13 and 14 which are arranged along a line L (see FIG. 2) perpendicular to the axis of rotation O so as to be opposite to each other with regard to the axis of rotation O.

Rods 21 and 22 are rigidly attached to support tables 23 and 24 at the lower surfaces thereof, respectively, and each of the rods 21 and 22 extends through these of the guiding slots 13 and 14. A spring, not shown, is provided between the side surfaces of the support tables 23 and 24 to cause them to normally move toward each other. Slit blades 31 and 32 are rigidly attached to the upper surfaces of the support tables 23 and 24, respectively.

The base plate 10 also has a groove forming portion 15 (see FIG. 1) for receiving a cam driving plate 42 so that the cam driving plate can be rotated about the axis of rotation O independently of the base plate 10. The cam driving plate 42 has an opening 42a at its central portion. The cam driving plate 42 is provided at its lower surface with a bevel gear 43. It should be noted that the gear faces both of the bevel gears 11 and 43 are formed along a conical plane generated to have a point P on the axis of rotation O as its apex. A cam plate 40 is attached to the upper surface of the bevel gear 43 by screws 45, 45' (see FIG. 2).

The cam plate 40 is formed with a central opening 41 and provided with cam surfaces 40a and 40b, each of which has a center of curvature in a position opposite to the other with regard to the axis of rotation O as a symmetrical axis. The above mentioned rods 21 and 22 are caused to engage the cam surfaces 40a and 40b, respectively.

The bevel gear 43 meshes with a bevel gear 61 while the bevel gear 11 meshes with a bevel gear 51. The gear faces of the bevel gears 51 and 61 are formed along a conical plane generated to have a point P on the axis of rotation O as its apex. A bearing 70 is attached to the casing K and a first drive shaft 52 is journaled within the bearing 70. The first drive shaft 52 has one end attached to the bevel gear 51 and the other end attached to a slit direction adjusting knob 53.

Furthermore, a second drive shaft 62 is coaxially journaled within the first drive shaft 52 and has one end attached to the bevel gear 61 and the other end attached to a slit width adjusting knob 63. The friction force between the second drive shaft 62 and the first drive shaft 52 is made to be less than that between the first drive shaft 52 and the bearing 70 or alternatively the friction force between the base plate 10 and the cam driving plate 42 is made to be less than that between the casing K and the base plate 10.

The slit apparatus according to the present invention operates as follows:

To begin with, the adjustment of slit direction will be explained. The slit direction adjusting knob 53 is rotated. The rotation of the slit direction adjusting knob 53 causes the bevel gear 51 and therefore the base plate 10 to rotate. The rotation of the base plate 10 about the axis of rotation O causes the slots 13 and 14 to angularly move around the axis of rotation O and thereby to cause the rods 21 and 22 received in the slots to angularly move around the axis of rotation O. The angular movement of the rods 21 and 22 in turn causes the slit blades 31 and 32 to rotate through the support tables 23 and 24. Thus, a slit or a gap between the slit blades 31 and 32 is caused to rotate about the axis of rotation O.

When the slit direction adjusting knob 53 is rotated as mentioned above, the second drive shaft 62 is caused to rotate in the same direction and degree as the knob 53 due to the friction between the first and second drive shafts 52 and 62 or between the base plate 10 and the cam driving plate 42, which then causes the bevel gear 61 to rotate. Simultaneously, the cam driving shaft 42 is rotated about the axis of rotation O by the same degree of angular movement of the base plate 10 about the axis of rotation O. Thus, the engagement points between the cam surfaces 40a, 40b of the cam plate 40 and the rods 21, 22 are not changed, that is, the slit width W is not changed while the direction of the slit is changed.

The adjustment of slit width will now be explained. The slit width adjusting knob 63 is rotated. Since the friction force between the first and second drive shafts 52 and 62 is less than that between the first drive shaft 52 and the bearing 70 or alternatively the friction force between the base plate 10 and the cam driving plate 42 is less than that between the base 10 and the casing K, the rotation of the knob 63 causes the second drive shaft 62 to rotate independently of the first drive shaft 52 to cause only the bevel gear 61 to rotate.

The rotation of the bevel gear 61 causes the cam driving plate 42 to rotate about the axis of rotation O and thereby to cause the cam plate 40 to rotate about the axis of rotation O. The rotation of the cam plate 40 is converted into linear movement of the rods 21, 22 on the line L, which in turn causes the slit blades 31 and 32 to move in opposite directions to each other through the support tables 23 and 24. Consequently, the slit width W is changed.

The adjustments of both the slit direction and slit width are independently made as described above.

The slit apparatus according to the invention has the advantages that the apparatus can be made compact and easy to operate by having the slit direction adjusting knob and the slit width adjusting knob arranged to be coaxial with each other.

I claim:

1. A slit apparatus which comprises a base plate (10) provided for rotation about an axis of rotation (O) and having a first gear (11) arranged along the direction of rotation: at least two guiding slots (13, 14) formed on said base plate (10) so that the slots are located in opposite positions with regard to said axis of rotation (O) and along a line (L) perpendicular to said axis of rotation (O); at least two rods (21, 22) movable along said guiding slots (13, 14), respectively; at least two slit blades (31, 32), each connected to one of the rods (21, 22) so that each of said slit blades is movable in a direction opposite to the other and in a direction parallel to said line (L); cam means (40, 42) having a second gear (43) arranged along the direction of rotation to cause each of said rods (21, 22) to move in a direction opposite to the other when said cam means is rotated about said axis of rotation; slit direction adjusting means comprising a first drive shaft (52) perpendicular to said axis of rotation (O), a first driving gear (51) meshing with said first gear (11), and a slit direction adjusting knob (53); and slit width adjusting means comprising a second drive shaft (62) coaxial with said first drive shaft (52), a second driving gear (61) meshing with said second gear (43), and a slit width adjusting knob (63).

* * * * *